(12) United States Patent
Cooper et al.

(10) Patent No.: US 9,662,175 B2
(45) Date of Patent: *May 30, 2017

(54) GIMBAL AND LEVERS WITH EQUALIZER

(71) Applicant: Intuitive Surgical Operations, Inc., Sunnyvale, CA (US)

(72) Inventors: Thomas G. Cooper, Menlo Park, CA (US); Anthony McGrogan, San Jose, CA (US); Matthew Reagan Williams, Walnut Creek, CA (US); Eugene F. Duval, Menlo Park, CA (US); S. Christopher Anderson, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 750 days.

This patent is subject to a terminal disclaimer.

(21) Appl. No.: 14/083,241

(22) Filed: Nov. 18, 2013

(65) Prior Publication Data

US 2014/0076076 A1 Mar. 20, 2014

Related U.S. Application Data

(63) Continuation of application No. 12/780,758, filed on May 14, 2010, now Pat. No. 8,603,077.

(51) Int. Cl.
*A61B 19/00* (2006.01)
*G05G 9/00* (2006.01)
(Continued)

(52) U.S. Cl.
CPC .......... *A61B 19/2203* (2013.01); *A61B 34/30* (2016.02); *A61B 34/71* (2016.02);
(Continued)

(58) Field of Classification Search
CPC .......... A61B 2017/00477; A61B 34/30; A61B 34/71; B25J 13/00; G05G 9/00
See application file for complete search history.

(56) References Cited

U.S. PATENT DOCUMENTS 4,919,112 A 4/1990 Siegmund
5,239,883 A 8/1993 Rosheim
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Gary Jackson
*Assistant Examiner* — Scott T Luan
(74) *Attorney, Agent, or Firm* — Blakely Sokoloff Taylor & Zafman LLP

(57) ABSTRACT

A force transmission includes a gimbal plate having two degrees of freedom. Each of three lever arms is supported by a pivot between two ends of the lever arm. One end of each lever arm is coupled to the gimbal plate such that the three couplings are not collinear. An equalizer cable has two opposing ends, each end fixedly coupled to one of the lever arms. The equalizer cable is routed over a lever arm pulley pivotally coupled to another of the lever arms between the pivot and one end of the lever arm. The gimbal plate may be coupled to the three lever arms by flexible cables or by links that transmit compression forces but not tension forces. The cables may be substantially contained within a tube. The links may be electrically non-conductive. The force transmission may control a surgical end effector in a teleoperated surgical instrument.

18 Claims, 5 Drawing Sheets

(51) Int. Cl.
  *B25J 13/00* (2006.01)
  *A61B 34/00* (2016.01)
  *A61B 34/30* (2016.01)
  *A61B 17/00* (2006.01)

(52) U.S. Cl.
  CPC ............... *B25J 13/00* (2013.01); *G05G 9/00* (2013.01); *A61B 2017/00477* (2013.01); *Y10T 74/18832* (2015.01); *Y10T 74/18856* (2015.01); *Y10T 74/20018* (2015.01); *Y10T 74/20323* (2015.01); *Y10T 74/20329* (2015.01)

(56) References Cited

U.S. PATENT DOCUMENTS

| | | | |
|---|---|---|---|
| 6,817,974 | B2 | 11/2004 | Cooper et al. |
| 7,320,700 | B2 | 1/2008 | Cooper et al. |
| 8,603,077 | B2 | 12/2013 | Cooper et al. |
| 2003/0036748 | A1* | 2/2003 | Cooper ............ A61B 17/00234 606/1 |
| 2008/0065102 | A1 | 3/2008 | Cooper |
| 2014/0076077 | A1 | 3/2014 | Cooper et al. |

\* cited by examiner

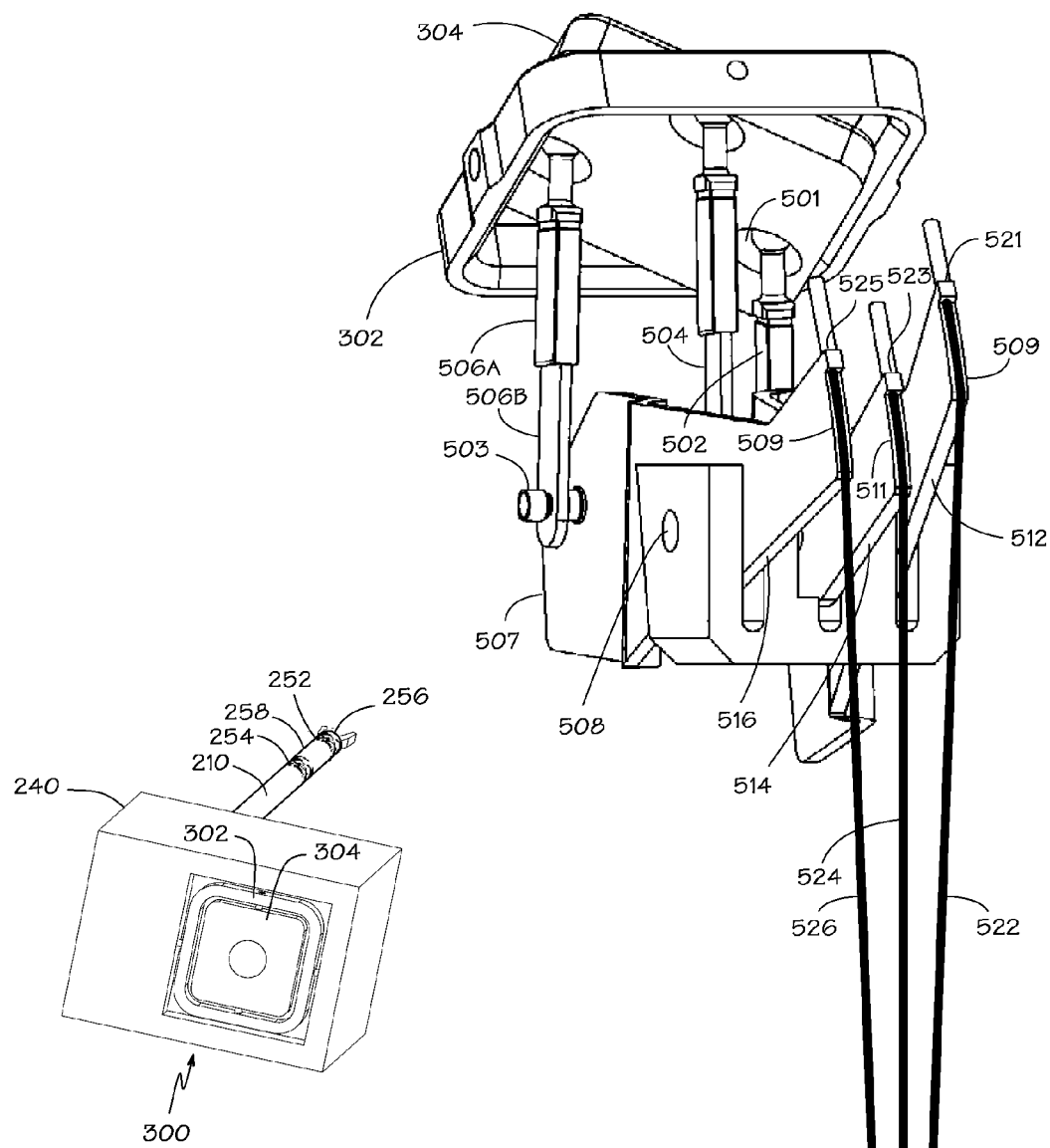
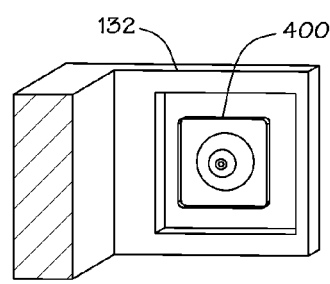
FIG. 3
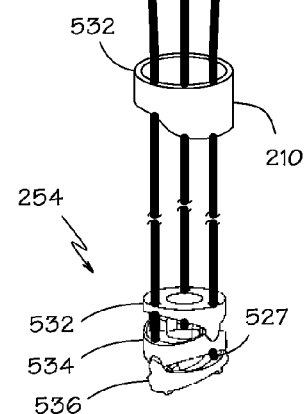
FIG. 4
FIG. 5

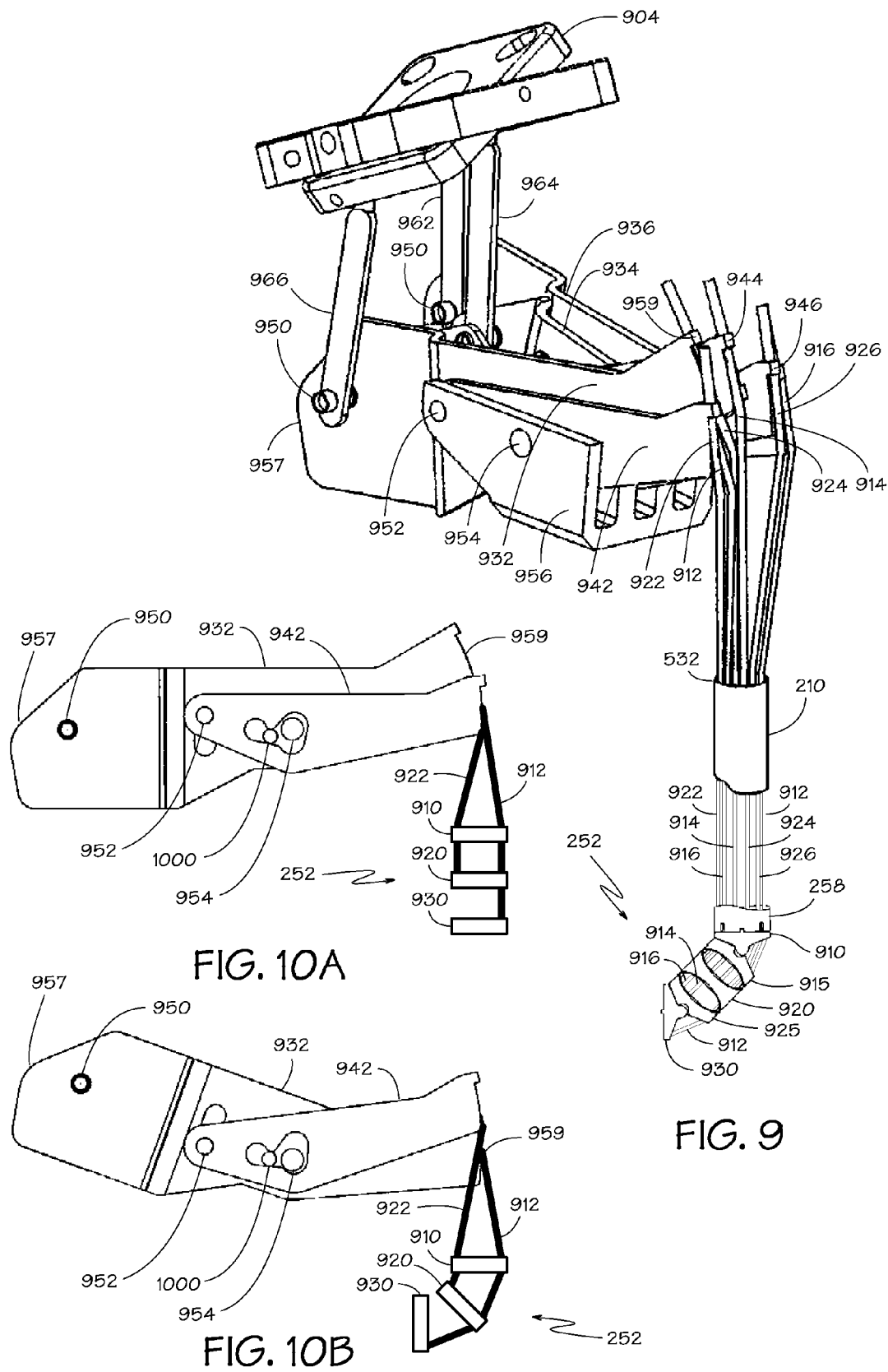

GIMBAL AND LEVERS WITH EQUALIZER

CROSS REFERENCE TO RELATED APPLICATIONS

This application is a continuation of application Ser. No. 12/780,758, filed May 14, 2010, which is hereby incorporated by reference in its entirety.

BACKGROUND

Field

Embodiments of the invention relate to the field of force transmissions; and more specifically, to force transmissions for use in surgical instruments intended for use in minimally invasive surgeries.

Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

The elongated surgical instruments will generally have an end effector in the form of a surgical tool such as a forceps, a scissors, a clamp, a needle grasper, or the like at one end of an elongate tube. The surgical tool is generally coupled to the elongate tube by one or more articulated sections to control the position and/or orientation of the surgical tool. An actuator that provides the actuating forces to control the articulated section is coupled to the other end of the elongate tube. A means of coupling the actuator forces to the articulated section runs through the elongate tube. Two actuators may be provided to control two articulated sections, such as an "arm" that positions the surgical tool and a "wrist" the orients and manipulates the surgical tool, with means for coupling both actuator forces running through the elongate tube.

It may be desirable that the elongate tube be somewhat flexible to allow the surgical instrument to adapt to the geometry of the surgical access path. In some cases, the articulated sections provide access to a surgical site that is not directly in line with the surgical access port. It may be desirable to use cables as the means of coupling the actuator forces to the articulated sections because of the flexibility they provide and because of the ability of a cable to transmit a significant force, a substantial distance, through a small cross-section. However, a cable is generally only able to transmit a force in tension. Thus it is generally necessary to provide two cables to transmit a bidirectional actuating force. This doubles the cross-section required for the cables to pass through the elongate tube.

In view of the above, it is desirable to provide an improved apparatus and method for transmitting bidirectional actuating forces through an elongate tube of a surgical instrument intended for use in minimally invasive surgeries that reduces the cross-section required in the elongate tube.

SUMMARY

A force transmission includes a gimbal plate having two degrees of freedom. Each of three lever arms is supported by a pivot between two ends of the lever arm. One end of each lever arm is coupled to the gimbal plate such that the three couplings are not collinear. An equalizer cable has two opposing ends, each end fixedly coupled to one of the lever arms. The equalizer cable is routed over a lever arm pulley pivotally coupled to another of the lever arms between the pivot and one end of the lever arm. The gimbal plate may be coupled to the three lever arms by flexible cables or by links that transmit compression forces but not tension forces. The cables may be substantially contained within a tube. The links may be electrically non-conductive. The force transmission may control a surgical end effector in a teleoperated surgical instrument.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 3 is a perspective view of the surgical instrument shown in FIG. 2.

FIG. 4 is a perspective view of a coupler portion of a teleoperated manipulator used with the surgical instrument shown in FIG. 2.

FIG. 5 is a simplified perspective view of a force transmission mechanism.

FIG. 9 is a simplified perspective view of another force transmission mechanism.

FIG. 10A is a portion of the force transmission mechanism shown in FIG. 9 in a first position.

FIG. 10B is a portion of the force transmission mechanism shown in FIG. 9 in a second position.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
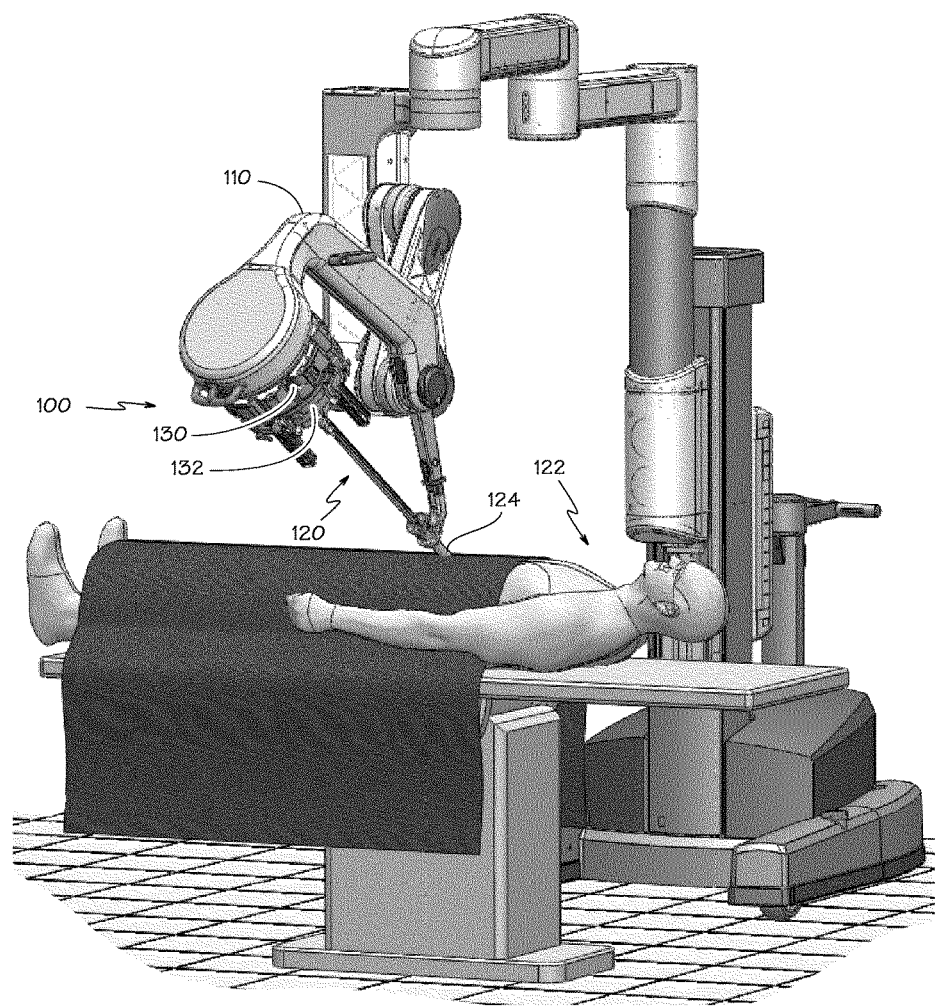
FIG. 1 is a simplified perspective view of a teleoperated surgical system with a remotely controlled surgical instrument inserted through a port in a patient's abdomen.

FIG. 1 is a simplified diagrammatic perspective view of a teleoperated surgical system 100, in accordance with embodiments of the present invention. The system 100 includes a support assembly 110 mounted to or near an operating table supporting a patient's body 122. The support assembly 110 supports one or more surgical instruments 120 that operate on a surgical site within the patient's body 122.

The term "instrument" is used herein to describe a device configured to be inserted into a patient's body and used to carry out surgical procedures. The instrument includes a surgical tool, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support for the surgical tool so that the position and orientation of the surgical tool can be manipulated.

The simplified perspective view of the system 100 shows only a single instrument 120 to allow aspects of the invention to be more clearly seen. A functional teleoperated surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, marketed by Intuitive Surgical, Inc., of Sunnyvale Calif.

A functional teleoperated surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control servo motors which, in turn, control the articulation of the surgical assembly. The forces generated by the servo motors are transferred via drivetrain mechanisms, which transmit the forces from the servo motors generated outside the patient's body 122 through an intermediate portion of the elongate surgical instrument 120 to a portion of the surgical instrument inside the patient's body 122 distal from the servo motor. Persons familiar with telemanipulative, teleoperative, and telepresence surgery will know of systems such as the da Vinci® Surgical System and the Zeus® system originally manufactured by Computer Motion, Inc. and various illustrative components of such systems.

The surgical instrument 120 is shown inserted through an entry guide 124, e.g., a cannula in the patient's abdomen. A functional teleoperated surgical system may provide an entry guide manipulator (not shown; in one illustrative aspect the entry guide manipulator is part of the support system 110) and an instrument manipulator (discussed below). The entry guide 124 is mounted onto the entry guide manipulator, which includes a positioning system for positioning the distal end of the entry guide 124 at the desired target surgical site. The positioning system may be provided in a variety of forms, such as a serial link arm having multiple degrees of freedom (e.g., six degrees of freedom) or a jointed arm that provides a remote center of motion (due to either hardware or software constraints) and which is positioned by one or more unpowered, lockable setup joints mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the teleoperated instrument manipulator 130. The teleoperated manipulator includes a coupler 132 to transfer controller motion from the teleoperated manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 2:
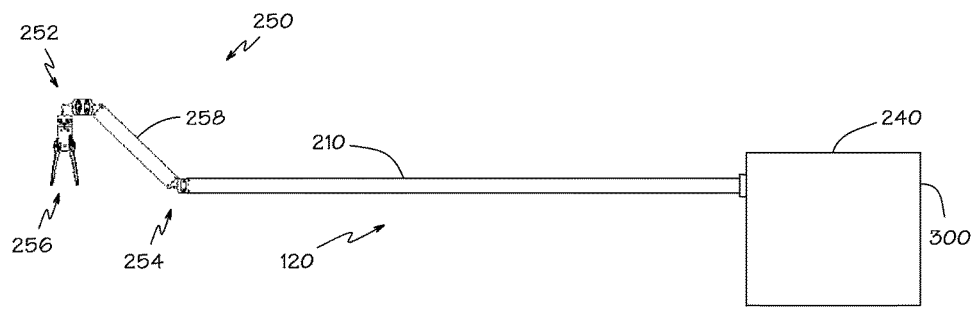
FIG. 2 is a plan view of a surgical instrument for use with a teleoperated manipulator.

FIG. 2 is a plan view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical devices such as the forceps 256 shown, a needle driver, a cautery device, a cutting tool, an imaging device (e.g., an endoscope or ultrasound probe), or a combined device that includes a combination of two or more various tools and imaging devices. In the embodiment shown, the surgical tool 256 is coupled to the elongate tube 210 by two articulated sections, a "wrist" 252 and a "joggle joint" 254, coupled by a tubular section 258 that allow the position and orientation of the surgical tool to be manipulated.

Surgical instruments that are used with the invention are controlled by a plurality of flexible cables. Cables provide a means of transmitting forces to the joints that is compact and flexible. A typical elongate tube 210 for a surgical instrument 120 is small, perhaps six millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale because forces and strengths of materials do not scale at the same rate as the size of the mechanisms. The cables must fit within the elongate tube 210 and be able to bend as they pass through the joints 252, 254 that offset the surgical tool 262.

FIG. 3 is a perspective view showing the proximal control mechanism 240 of the surgical instrument 120 in more detail. In this embodiment, a gimbal assembly 300 is provided to receive a controlling input. The gimbal assembly includes an outer gimbal 302 that is pivotally supported by a housing of the proximal control mechanism and an inner gimbal 304 that is pivotally supported by the outer gimbal. The axes of the inner and outer gimbal assemblies intersect and allow the inner gimbal assembly to move with two degrees of rotational freedom, one for each of the two axes of the gimbal assembly. The inner gimbal has a center of rotation at the intersection of the inner and outer axes. U.S. patent application Ser. No. 12/060,104, which is incorporated herein in its entirety, discloses couplers for providing the controlling input.

The articulated sections 252, 254 (FIG. 2) of the surgical instruments are also gimbals, each having two degrees of rotational freedom. Thus it is possible to control the movement of the articulated sections 252, 254 by copying the motion of the input at the inner gimbal 304 to the output at the output gimbal of the articulated sections. It will be appreciated that the input gimbal is substantially larger than the output gimbal in the embodiment shown. Therefore it is desirable to use a force transmission apparatus that scales the motions of the input gimbal to provide motions that are appropriate for controlling the output gimbal. The mechanisms that provide the controlling motions to the input gimbal are generally bulky while it is necessary for the output gimbals to be compact and located in close proximity to one another. Therefore it is desirable to use a force transmission apparatus that spatially translates the motions of the input gimbals to allow the output gimbals to be closely packed.

FIG. 4 shows a perspective view of the coupler portion 132 of the teleoperated manipulator 130. The coupler 132 includes a plate 400 that bears against the inner gimbal 304 of the gimbal assembly 300 in the proximal control mechanism 240 of the surgical instrument 120 when the instrument is connected to the teleoperated manipulator 130. The forces applied to the inner gimbal 304 by the plate 400 control movements of the surgical instrument 120.

FIG. 5 shows a simplified perspective view of a force transmission mechanism that transfers the forces applied on the inner gimbal 304 to one of the articulated sections 254 at a distal end of the elongate tube 210. The inner gimbal 304 acts as an input gimbal plate having two degrees of freedom. The input gimbal plate is coupled to three lever arms 512, 514, 516 by three coupler links 502, 504, 506.

In the embodiment shown, each coupler link includes an inner link 506A that slides within an outer link 506B. This allows the link 506 to transmit an downward movement of the inner gimbal 304 by pressing on the link. When the inner gimbal 304 moves up, the outer link 506B slides over the inner link 506A preventing the link 506 from transmitting an upward movement of the inner gimbal. Part of the link, preferably the outer link 506B, may be made of a non-conductive material, such as plastic, to electrically isolate the inner gimbal 304 from the surgical instrument 120.

Each lever arm is supported by a pivot 508 between a first end 507 and a second end 509 of the lever arm. A first end 503 of each of the coupler links is pivotally coupled to the first end of one of the lever arms 512, 514, 516. A second end 501 of each of the coupler links is pivotally coupled to the input gimbal plate 304, such as by a ball and socket connection. The second ends of the coupler links are not collinear so that any change in the position of the input gimbal plate 304 will move at least one of the coupler links.

The articulated section 254 at the distal end of the elongate tube 210 provides two degrees of angular freedom. Three output links 522, 524, 526, such as flexible cables, are coupled to a plate at the distal end of the articulated section 254 at a first end 527 of the output link and coupled to the second end of one of the lever arms 516 at a second end 525 of the output link. In the embodiment shown in FIG. 2, the articulated section 254 moves the tubular section 258 to position the surgical tool 256 within the surgical site.

A first end 532 of the elongate tube 210 is adjacent the lever arms 512, 514, 516, which are part of the proximal control mechanism 240. The output links 522, 524, 526 are substantially contained within the tube 210 with the links extending from the opposing ends of the tube to connect to the lever arms and the articulated sections. Any force applied to move the input gimbal plate 304 will be transmitted to move the output gimbal plate 536 to a corresponding position because the three non-collinear connections to each gimbal plate define a unique orientation of each gimbal plate. It will be appreciated that while the output plate 536 is described as a gimbal plate because it has two degrees of angular freedom, the embodiment shown is not a true gimbal because the axes of rotation for the plate do not intersect and do not lie in the same plane as the plate. The small scale of the joint makes it difficult to construct the joint as a true gimbal. Nonetheless, the output plate 536 does track the movements of the input gimbal plate 304 and it is therefore helpful to consider the output plate as the output gimbal plate.

The connections to the gimbal plates are arranged so that for each axis of rotation, there are connections on both sides of the axis that are spaced substantially away from the axis. Thus any movement of the input gimbal plate 304 will create tension in at least one of the three output links 521, 523, 525. That tension will cause the output gimbal plate 536 to move and apply tension to any of the three output links 522, 524, 526, that are not in tension from movement of the input gimbal plate 304. Flexible cables can be used for the output links because the operation of the force transmission maintains tension in all the output links under most operating conditions. However, under some load conditions one or more output links can go slack. Using coupler links that include an inner link 506A that slides within an outer link 506B prevents movement of the input gimbal plate 304 from unloading the output links.

Figure 6:
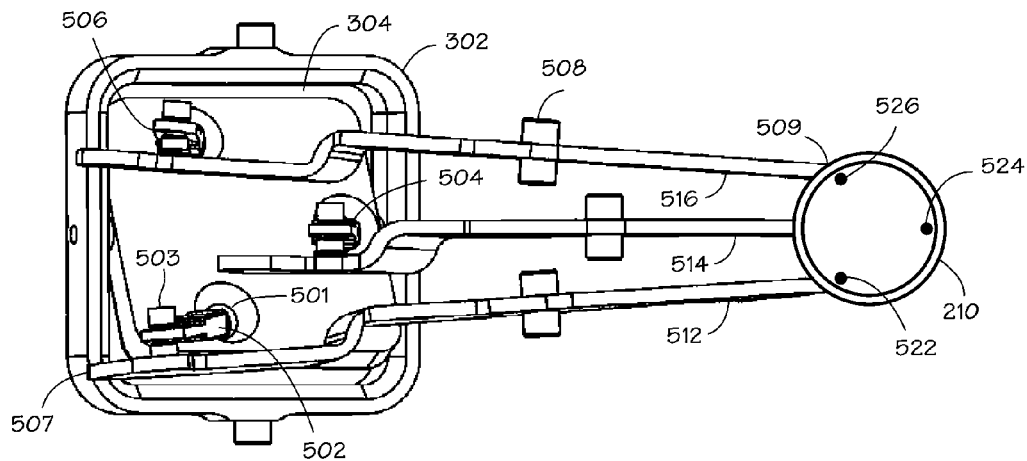
FIG. 6 is a bottom view of a portion of the force transmission mechanism shown in FIG. 5.

FIG. 6 is a bottom view of a portion of the force transmission mechanism shown in FIG. 5. In this embodiment, it will be seen that a first distance between adjacent first ends 503 of the coupler links 502 is greater than a second distance between adjacent second ends 521 of the output links 522. This allows a larger actuator to be used to apply force to a larger input gimbal plate 304 relative to the size of the output gimbal plate 536 and the elongate tube 210 which are 5 to 6 mm in diameter in the embodiment shown.

Figure 7:
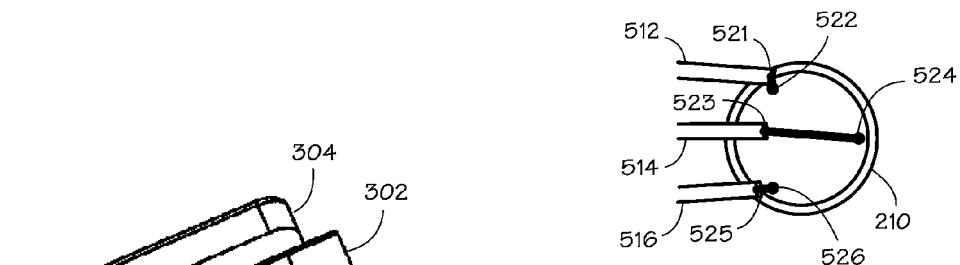
FIG. 7 is a top view of a portion of the force transmission mechanism shown in FIG. 5.

FIG. 7 is a top view of a portion of the force transmission mechanism shown in FIG. 5. FIGS. 6 and 7 show how the cables are routed from the ends 509 of the lever arms 512, 514, 516 into the top 532 of the elongate tube 210. In the embodiment shown, the cables are substantially equally spaced around the outer perimeter of the tube 210 which allows a maximum force to be applied to the output gimbal plate.

Figure 8:
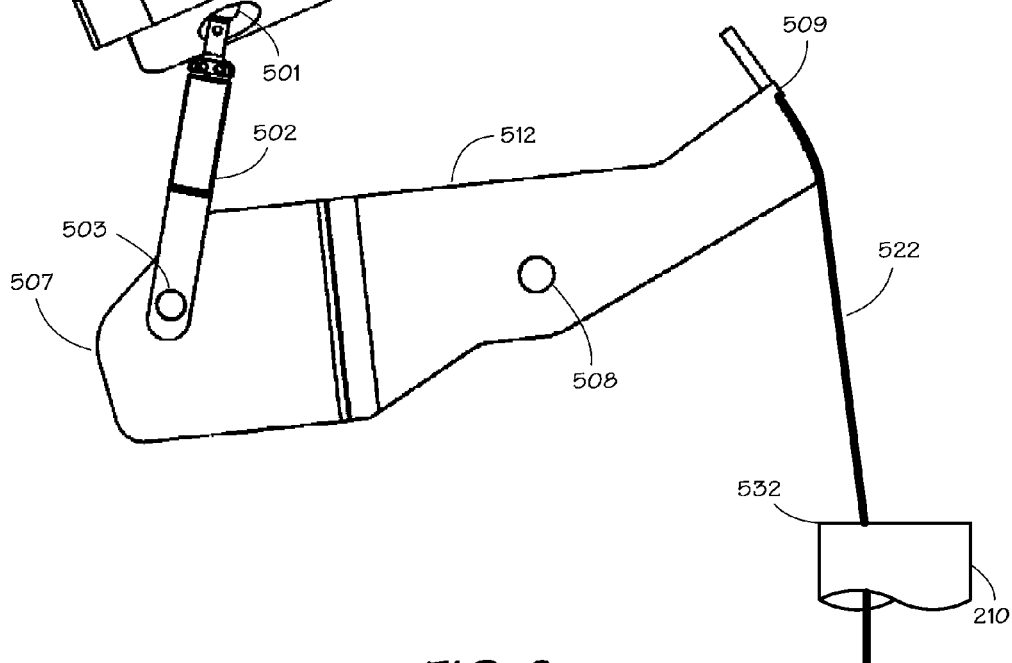
FIG. 8 is a side view of a portion of the force transmission mechanism shown in FIG. 5.

FIG. 8 is a side view of a portion of the force transmission mechanism shown in FIG. 5. Only one coupler link 502, lever arm 512, and output link 522 are shown to allow the arrangement of the coupling of these parts to be clearly seen. It will be appreciated that the location of the pivot 508 that supports the lever arm 512 can be chosen to provide various ratios of movement and force between the first end 503 of the coupler link 502 and the second end 521 of the output link 522.

FIG. 9 shows a simplified perspective view of another force transmission mechanism that transfers the forces applied on an inner gimbal 904 to an articulated section 252 at a distal end of the elongate tube 210. In this embodiment, the articulated section 252 is a "wrist" that supports the surgical tool 256. The wrist 252 is coupled to the distal end of the tubular section 258, which allows the wrist to be positioned adjacent the surgical site.

The articulated section 252 acts as an output gimbal plate having two degrees of angular freedom coupled to a secondary output gimbal plate having two degrees of angular freedom. The articulated section 252 in the embodiment shown includes five segments. Each pair of segments is coupled such that the segments of the pair can rotate (e.g., pitch or yaw) relative to one other around a single axis. Three adjacent segments act as a gimbal plate because the two axes of the two pairs of segments are orthogonal to one another. The three segments 920, 925, 930 farthest from the distal end of the elongate tube 210 act as the output gimbal plate. The first segment 920 of the output gimbal plate along with the two segments 925, 930 closest to the distal end act as the secondary output gimbal plate.

The use of two stacked gimbals permits a greater range of angular movement and provides a greater radius of curvature for the articulation of the wrist. The secondary output gimbal plate moves to a first angle that is a portion of the total angle of the wrist movement and the output gimbal plate moves the remainder of the total angle. In the embodiment shown, the secondary output gimbal plate moves through one-half of the total angle and the output gimbal plate moves through the same amount relative to the secondary output gimbal plate to provide the total angle of movement.

The input gimbal plate 904 is coupled to three lever arms 932, 934, 936 by three coupler links 962, 964, 966. Each lever arm is supported by a pivot 954 between a first end 957 and a second end 959 of the lever arm. A first end 950 of each of the coupler links is pivotally coupled to the first end 957 of one of the lever arms 932, 934, 936. A second end of each of the coupler links is pivotally coupled to the input gimbal plate 904, such as by a ball and socket connection. The second ends of the coupler links are not collinear so that any change in the position of the input gimbal plate 904 will move at least two of the coupler links in opposite directions.

Three output links 912, 914, 916, such as flexible cables, are coupled to the output gimbal plate 930 at a first end of the output links and coupled to the second end 959 of the lever arms 932, 934, 936 at a second end of the output links. The output gimbal plate 930 moves in response to movements of the input gimbal plate 904 in substantially the same way as described above for the embodiment shown in FIGS. 5-8.

Three secondary levers 942, 944, 946 are provided to control three secondary output links 922, 924, 926. Each of the secondary output links has a first end coupled to the secondary output gimbal plate 920 and a second end coupled to one of the secondary levers. The secondary output links 922, 924, 926 are arranged to move the secondary output links 922, 924, 926 with a motion that is proportional to the motion of the associated output links 912, 914, 916. In the embodiment shown, each secondary output link moves one-half the distance of the associated output link in the opposite direction. The secondary output link is coupled to the secondary output gimbal plate 920 at a point that is diametrically opposite the point where the output link for the associated output link is coupled to the output gimbal plate 930. This causes the secondary output gimbal plate 920 to move through half the angle of the output gimbal plate 930. Both gimbals move in the same direction because the diametrically opposed attachments cancel the effect of the opposite directions of motion at the levers.

Each secondary lever 942, 944, 946 is supported by a secondary pivot 952. The pivots 954 that support the lever arms 932, 934, 936 and the secondary pivots 952 that support the secondary levers 942, 944, 946 are supported by a ground frame 970 that is in a fixed relationship to the elongate tube 210. The ground frame 956 provides the frame of reference for the movements of the force transmission mechanism.

FIGS. 10A and 10B show one of the lever arms 932 and one of the secondary levers 942 associated with the lever arm with a schematic representation of the articulated section 252. The ground frame 956 has been omitted for clarity to show how the mechanism works. It is helpful to remember when viewing FIGS. 10A and 10B that lever arm 932 pivots around pivot 954, secondary lever 942 pivots around pivot 952, and both pivots 952 and 954 are fixed with reference to one another in the ground frame 956. FIG. 10A shows the lever arm 932 and the secondary lever 942 in a first position where the articulated section 252 is straight. FIG. 10B shows the lever arm 932 in a second position where a force on the first end 950 of the coupler link (not shown) has raised the first end 957 of the lever arm 932. This causes the second end 959 of the lever arm 932 to be lowered, extending the output link 912 that is coupled to the second end of the lever arm 932.

It will be appreciated that the output link 912 may be flexible and unable to transmit a significant force in compression. However, at least one of the remaining two output links 914, 916 will be retracted because the connections to the gimbal plates are arranged so that for each gimbal axis of rotation, there are connections on both sides of the gimbal axis that are spaced substantially away from the gimbal axis. Thus, when an output link is extended, the output gimbal plate will be moved by another output link that is retracted and applies tension to the extended output link.

Each secondary lever 942 is supported by the secondary pivot 952 at a first end of the secondary lever. A secondary output link 922 is coupled to a second end of the secondary lever 942. A force applying connector 1000 is fixed to the lever arm 932 and is coupled to the secondary lever 942 associated with the lever arm 932 to apply a force to the secondary lever when the lever arm 932 is moved.

In the embodiment shown, the force applying connector 1000 applies force to the secondary lever 942 at a point that is between the pivot 952 and the load of the secondary output link 922, making the secondary lever a third class lever. The force applying connector 1000 is fixed to the lever arm 932 between the pivot 954 that supports the lever arm and the second end 950 of the coupler link 966 that is coupled to the lever arm. The portion of the lever arm 932 that applies the force to the secondary lever 942 therefore acts as a second class lever.

Since the overall lever arm 932 is a first class lever, where the applied force moves the load in the opposite direction, the force applying connector 1000 moves in the same direction as the applied force and in the opposite direction as the output link 912. Since the secondary lever 942 is a third class lever, the force applied by the force applying connector 1000 moves the load of the secondary output link 922 in the same direction as the motion of the force applying connector and in the opposite direction as the output link 912. In the embodiment shown, the secondary levers are configured so that the output displacement of the secondary levers is half the output displacement of the lever arms to meet the requirements of the articulated wrist section 252. In other embodiments, the output displacement of the secondary lever may be configured to have other relationships to the output displacement of the lever arm.

Figure 11:
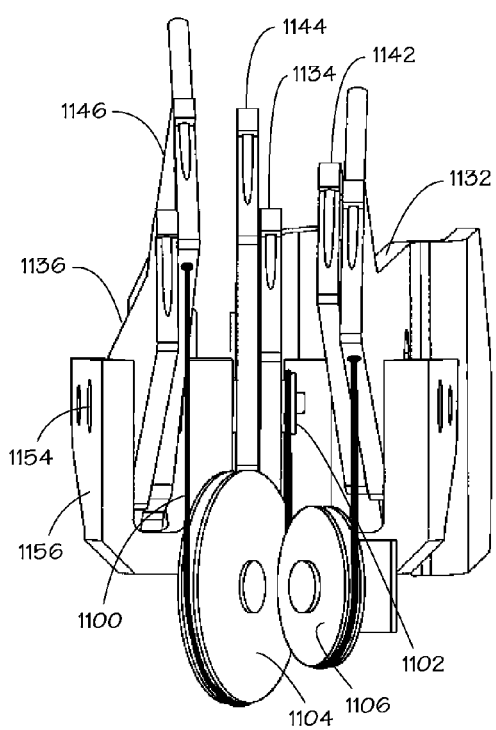
FIG. 11 is a front view of a portion of still another force transmission mechanism.
Figure 12:
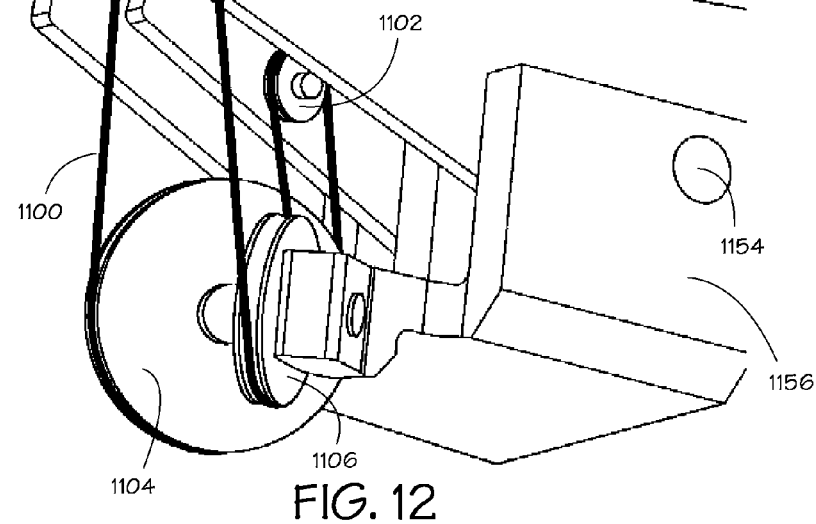
FIG. 12 is an oblique view of the force transmission mechanism of FIG. 11.

FIGS. 11 and 12 show a front and oblique views of a portion of another force transmission mechanism. As in the embodiment shown in FIGS. 9 and 10, this embodiment includes secondary levers 1142, 1144, 1146 that are moved in an opposite direction by movement of primary lever arms 1132, 1134, 1136. The output links that are connected to the ends of these lever arms are not shown to allow others aspects to be seen more clearly.

As the primary lever arms 1132, 1134, 1136 are moved, they cause the secondary levers 1142, 1144, 1146 to move in an opposite direction. This can apply forces to the primary levers that limits their range of motion. An equalizer cable 1100 can link the primary lever arms 1132, 1134, 1136 at the driven ends to overcome the additional forces on the primary levers from the interaction with the secondary levers 1142, 1144, 1146. The equalizer cable 1100 is coupled to the two outside primary levers 1132, 1136 and routed over a lever arm pulley 1102 supported by the primary lever arm 1134 that is between the outside primary lever arms. Two idler pulleys 1104, 1106 route the cable from the lever arm pulley 1102 to the outside primary levers 1132, 1136. The equalizer cable 1100 can be arranged to provide a kinematic constraint on the motion of the driven ends of the primary lever arms 1132, 1134, 1136 because these motions are coupled by the gimbal plate (not shown) that drives the three primary lever arms.

Figure 13:
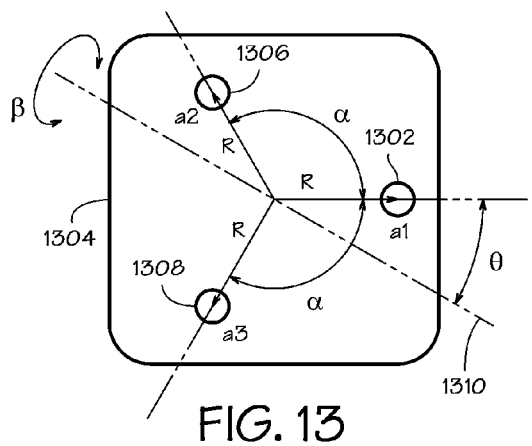
FIG. 13 is a plan view of an input gimbal.

FIG. 13 is a plan view of a gimbal plate 1304 that drives the primary levers 1132, 1134, 1136 (FIGS. 11 and 12). The input gimbal plate 1304 is coupled to the primary levers 1132, 1134, 1136 by three coupler links (not shown). The coupler links are attached to the gimbal plate at three points 1302, 1306, 1308 that are not collinear so that any change in the position of the input gimbal plate 1304 will move at least two of the coupler links and the primary levers they drive in opposite directions. For example, if the gimbal plate is rotated about the axis that runs through the point 1302 where one of the coupler links is attached to the gimbal plate, the remaining two coupler links move in opposite directions. As another example, if the gimbal plate is rotated about the axis line indicated by reference numeral 1310, the two coupler links attached to points 1302, 1306 on one side of the axis will move in one direction and the coupler link attached to the points 1308 on the other side of the axis will move in the opposite direction.

In the embodiment shown, the three points 1302, 1306, 1308 of attachment for the coupler links are equidistant from the center of motion of the input gimbal plate 1304. The distance from the center of motion to the points of attachment is represented by the distance R. The three points 1302, 1306, 1308 of attachment are spaced apart equally so that the angle α between the lines connecting center of motion and two points of attachment is 120°. If the input gimbal plate 1304 is rotated about an arbitrary axis 1310 through an angle β, each point of attachment will be displaced by a distance $$a = \beta R \sin \phi$$

where $\phi$ is the angle between the axis 1310 and the line connecting the center of motion and the point of attachment. If the angle between the axis 1310 and the line connecting the center of motion and a first point of attachment 1302 is θ, then the angles for the other two points of attachment 1306, 1308 are (θ+α) and (θ−α). Therefore the displacements for the three points 1302, 1306, 1308 of attachment are $$a1 = \beta R \sin \theta$$

$$a2 = \beta R \sin(\theta + \alpha)$$

$$a3 = \beta R \sin(\theta - \alpha)$$

Using the trigonometric identity of $$\sin(a+b) = \sin a \cos b + \cos a \sin b$$

the sum of the displacements for the three points 1302, 1306, 1308 of attachment is $$a1 + a2 + a3 = \beta R(\sin \theta + \sin \theta \cos \alpha + \cos \theta \sin \alpha + \sin \theta \cos \alpha + \cos \theta \sin(-\alpha))$$

This can be rewritten as $$a1 + a2 + a3 = \beta R[\sin \theta(1 + \cos \alpha + \cos(-\alpha)) + \cos \theta(\sin \alpha + \sin(-\alpha))]$$

Since α is 120°, $$\cos \alpha = \cos -\alpha = -0.5$$

$$\sin \alpha = 0.886$$

$$\sin -\alpha = -0.886$$

The sum of the displacements for the three points 1302, 1306, 1308 of attachment therefore simplifies to $$a1 + a2 + a3 = \beta R[\sin \theta(1 - 0.5 - 0.5) + \cos \theta(0.886 - 0.886)] = 0$$

Figure 14:
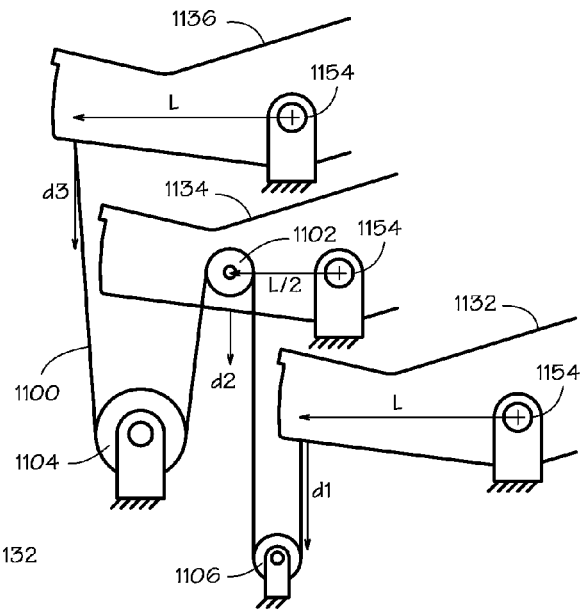
FIG. 14 is a schematic representation of the force transmission mechanism of FIG. 11.

FIG. 14 is a schematic representation of the primary levers 1132, 1134, 1136, the pulleys 1102, 1104, 1106, and the equalizer cable 1100. Each primary lever arm is supported by a pivot 1154. In the embodiment shown, the primary levers 1132, 1134, 1136 are supported by a common pivot shaft 1154 that is supported by a common ground frame 1156. In other embodiments, each primary lever is supported by its own pivot that is supported by a common ground frame. The two idler pulleys 1104, 1106 are pivotally supported by the common ground frame 1156. The lengths of the equalizer cable 1100 segments between each of the primary levers 1132, 1134, 1136 and the grounded idler pulleys 1104, 1106 changes as the levers move. The displacements of the lever outputs are indicated as d1, d2, and d3 in FIG. 14. The net change of length in the equalizer cable 1100 due to the displacements of the lever outputs is $$d1+2d2+d3$$

where the displacement d2 is doubled because of the effect of the pulley 1102.

For the embodiment shown, the two ends of the equalizer cable 1100 are fixed to the two outer primary levers 1132, 1136 at a distance L from the pivot 1154. The pulley 1102 on the middle primary levers 1134 is pivotally supported at a distance L/2 from the pivot 1154. The output displacement d of a first class lever is related is related to the input displacement a by $$d/L=-a/X$$

where L is the distance between the fulcrum or pivot of the lever and the point of the output displacement and X is the distance between the fulcrum and the point of the input displacement. Since L and X are the same for all primary levers in the embodiment shown $$d1=-a1L/X$$

$$d2=-a2L/2X$$

$$d3=-a3L/X$$

The net change of length in the equalizer cable 1100 is therefore $$-a1L/X+2(-a2L/2X)+(-a3L/X)$$

This can be rewritten as $$-L/X(a1+a2+a3)$$

Since it was previously shown that $$a1+a2+a3=0$$

for the embodiment shown, the movement of the primary levers 1132, 1134, 1136 does not change the length of the equalizer cable 1100. Therefore, the equalizer cable 1100 provides a kinematic constraint to maintain the proper relationship between the output ends of the primary levers 1132, 1134, 1136 by transferring upward forces in the outputs of the primary levers to downward forces on the remaining primary levers.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A force transmission comprising:
a gimbal plate having two degrees of freedom;
three lever arms, each lever arm supported by a pivot between two ends of the lever arm, one end of each of the three lever arms coupled to the gimbal plate such that the three couplings are not collinear; and
an equalizer cable having two opposing ends, each end fixedly coupled to a first and a second of the three lever arms, the equalizer cable being routed over a lever arm pulley pivotally coupled to a third of the three lever arms between the pivot and one end of the third lever arm.

2. The force transmission of claim 1 further comprising three coupler links, each coupler link coupling of one of the three lever arms to the gimbal plate.

3. The force transmission of claim 2 wherein each of the three coupler links comprises a flexible cable.

4. The force transmission of claim 3 further comprising a tube having a first end adjacent the three lever arms and an opposing second end adjacent a surgical end effector wherein each of the three coupler links are substantially contained within the tube.

5. The force transmission of claim 2 wherein each of the three coupler links comprises an inner link that slides within an outer link such that each of the three coupler links transmits compression forces and does not transmit tension forces.

6. The force transmission of claim 2 wherein part of each of the three coupler links is made of an electrically non-conductive material.

7. A force transmission for a teleoperated surgical instrument comprising:
an input gimbal plate having two degrees of freedom;
three lever arms, each lever arm supported by a pivot between two ends of the lever arm, one end of each of the three lever arms coupled to the input gimbal plate such that the three couplings are not collinear;
three output links, each output link having a first end coupled to an articulated joint that supports a surgical end effector and a second end coupled to one of the three lever arms; and
an equalizer cable having two opposing ends, each end fixedly coupled to a first and a second of the three lever arms, the equalizer cable being routed over a lever arm pulley pivotally coupled to a third of the three lever arms between the pivot and one end of the third lever arm.

8. The force transmission of claim 7 wherein each of the three output links comprises a flexible cable.

9. The force transmission of claim 8 further comprising a tube having a first end adjacent the three lever arms and an opposing second end adjacent the surgical end effector wherein the three output links are substantially contained within the tube.

10. The force transmission of claim 7 further comprising three coupler links, each coupler link coupling of one of the three lever arms to the input gimbal plate.

11. The force transmission of claim 10 wherein each of the three coupler links comprises an inner link that slides within an outer link such that each of the three coupler links transmits compression forces and does not transmit tension forces.

12. The force transmission of claim 10 wherein part of each of the three coupler links is made of an electrically non-conductive material.

13. The force transmission of claim 7 wherein a first distance between adjacent ends of the three lever arms that are coupled to the input gimbal plate is greater than a second distance between adjacent ends of the three lever arms that are coupled to the three output links.

14. A force transmission comprising:
an input gimbal means for receiving an input force having two degrees of freedom;
three lever arms, each lever arm supported by a pivot;
three coupler means for coupling the input gimbal means to the three lever arms; and
an equalizer means for providing a kinematic constraint on motion of the three lever arms.

15. The force transmission of claim 14 further comprising
an output gimbal means for delivering the input force with two degrees of freedom; and
three output link means for coupling the three lever arms to the output gimbal means.

16. The force transmission of claim 15 further comprising a tube means for substantially containing the three output link means.

17. The force transmission of claim 15 wherein the output gimbal means is further for supporting a surgical end effector.

18. A method of transmitting force to a teleoperated surgical instrument, the method comprising:
receiving a force with an input gimbal plate having two degrees of freedom;
transferring the force to an end of each of three lever arms, each of the three lever arms supported by a pivot;
transferring the force from an opposite end of each of the three lever arms to an articulated joint that supports a surgical end effector; and
providing a kinematic constraint on motion of the three lever arms with an equalizer cable.

\* \* \* \* \*